(12) United States Patent
Hofen et al.

(10) Patent No.: US 7,157,610 B2
(45) Date of Patent: Jan. 2, 2007

(54) PROCESS FOR RECOVERING METHANOL

(75) Inventors: Willi Hofen, Rodenbach (DE); Thomas Haas, Frankfurt (DE); Bärbel Kolbe, Witten (DE)

(73) Assignees: Degussa AG, Düsseldorf (DE); Uhde GmbH, Dortmund (DE)

( * ) Notice: Subject to any disclaimer, the term of this patent is extended or adjusted under 35 U.S.C. 154(b) by 0 days.

(21) Appl. No.: 11/312,237

(22) Filed: Dec. 19, 2005

(65) Prior Publication Data

US 2006/0135826 A1 Jun. 22, 2006

Related U.S. Application Data

(60) Provisional application No. 60/638,365, filed on Dec. 20, 2004.

(30) Foreign Application Priority Data

Dec. 21, 2004 (DE) .................. 10 2004 061 352

(51) Int. Cl.
*C07C 29/80* (2006.01)
*C07C 29/82* (2006.01)
*C07C 29/74* (2006.01)

(52) U.S. Cl. .................. 568/918; 568/913; 203/38; 203/78; 203/80

(58) Field of Classification Search .................. 568/918, 568/913; 203/38, 78, 80
See application file for complete search history.

(56) References Cited

U.S. PATENT DOCUMENTS

| 4,659,866 A | 4/1987 | Bott et al. |
| 2003/0040637 A1 | 2/2003 | Hofen et al. |
| 2003/0144535 A1 | 7/2003 | Teles et al. |

FOREIGN PATENT DOCUMENTS

| EP | 1 293 505 A1 | 3/2003 |
| EP | 1 424 332 A1 | 6/2004 |
| RU | 2 159 664 C1 | 11/2000 |
| WO | WO 02/02544 A1 | 1/2002 |

*Primary Examiner*—Elvis O. Price
(74) *Attorney, Agent, or Firm*—Smith, Gambrell & Russell, LLP

(57) ABSTRACT

A process for recovering methanol from mixtures containing methanol and water, comprising multistage evaporation with heat integration, wherein the pressure is reduced from each stage to the next, and a downstream series of distillation stages with heat integration, wherein the pressure is increased from each stage to the next. The process reduces the amount of energy required for methanol recovery.

9 Claims, 1 Drawing Sheet

PROCESS FOR RECOVERING METHANOL

REFERENCES TO RELATED APPLICATION

This application claims the benefit of provisional application 60/638,365 filed Dec. 20, 2004, and Germany priority application 10 2004 061 352.4 filed Dec. 21, 2004, which are relied on and incorporated herein by reference.

INTRODUCTION AND BACKGROUND

The invention relates to an improved process for recovering methanol from mixtures containing methanol and water, which process requires less energy for separation.

Propylene oxide may be produced by reacting propylene with hydrogen peroxide in the presence of a titanium-containing zeolite catalyst. Methanol is advantageously used as solvent in this process. When working up the reaction mixture resulting from this process, a mixture is obtained which contains methanol and water. Methanol has to be recovered from this mixture, in order to be able to return it to the epoxidation reaction and to be able to operate the process economically. The water arising from hydrogen peroxide and any water introduced into the process with aqueous hydrogen peroxide, has to be removed from the process. The recovery of methanol from the mixture containing methanol and water consumes a large proportion of the thermal energy expended on the process. To perform the process economically, there is therefore a need for an improved process for recovering methanol from a mixture containing methanol and water, wherein the method exhibits a reduced energy requirement.

WO 02/02544 describes a process for the production of propylene oxide, in which working up of the reaction mixture results in a mixture which contains methanol, water and small quantities of hydrogen peroxide. The document describes separating off water from this mixture by distillation performed in two columns, wherein the pressures are so selected that the bottom of the column operated at low pressure is heated using the vapors from the second column, which is operated at high pressure. The coupling of the columns described in WO 02/02544 makes it possible to reduce the energy requirement for recovering methanol from the mixture.

However, the need still remains for processes for recovering methanol which require less energy than the prior art. This object is achieved by the process according to the invention.

SUMMARY OF THE INVENTION

The present invention provides a process for recovering methanol from mixtures containing methanol and water, wherein the process comprises multistage evaporation and a downstream series of distillation stages and wherein the bottoms obtained in the final evaporation stage of the multistage evaporation are supplied to the first distillation stage of the series of distillation stages. The multistage evaporation comprises at least two evaporation stages, wherein each evaporation stage comprises an evaporator and, in the multistage evaporation, the pressure is reduced from each evaporation stage to the next evaporation stage. The evaporator of the second and each subsequent evaporation stage is heated with the vaporous overhead of the in each case previous stage. The series of distillation stages comprises at least two distillation stages, wherein each distillation stage comprises a distillation column and an evaporator and wherein the bottoms from the in each case previous distillation stage are supplied to the second and each subsequent distillation stage. In the series of the distillation stages, the pressure is increased from each distillation stage to the next distillation stage and, with the exception of the final distillation stage, in each distillation stage the evaporator is heated in each case with the vaporous overhead of the distillation column of the subsequent distillation stage.

Preferably, each evaporation stage additionally comprises a distillation column with a rectifying section, such that an overhead with a methanol content of more than 90 wt. %, preferably more than 95 wt. %, is obtained in each evaporation stage.

BRIEF DESCRIPTION OF DRAWING

The drawing represents a flow chart of a preferred embodiment of the method of the invention.

DETAILED DESCRIPTION OF INVENTION

Figure 1:
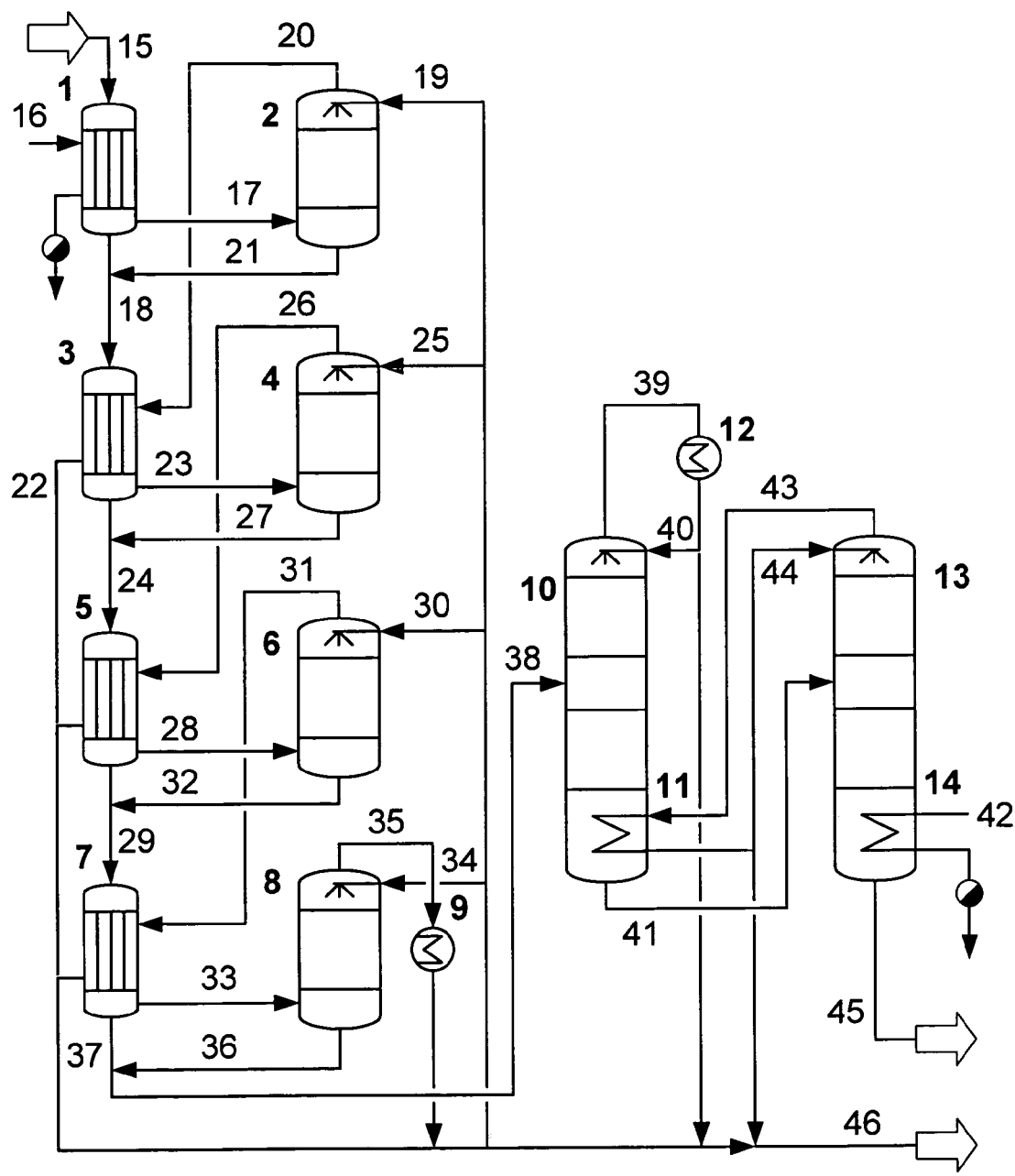

The process according to the invention comprises multistage evaporation with at least two evaporation stages, wherein the pressure is reduced from each evaporation stage to the next. Each of the evaporation stages comprises an evaporator, wherein any evaporator may be used for the process according to the invention which is suitable for evaporation of methanol from mixtures containing methanol and water. Preferably, continuous-flow evaporators are used in the evaporation stages, which evaporators may be operated without a circulating pump. In each evaporation stage, the mixture is supplied in liquid form to the evaporator and vaporous vapors and liquid bottoms are obtained as a result of evaporation. The liquid bottoms are supplied in each case to the evaporator of the next evaporation stage. Due to the reduction in pressure from each evaporation stage to the next, no pump is generally necessary for this purpose.

The evaporator of the first evaporation stage is heated with a heating medium, preferably with steam. The evaporator of the second and each subsequent condensation stage is heated with the vapors, i.e. the vaporous overhead, of the in each case previous stage.

The number of evaporation stages is selected in accordance with the composition of the mixture from which methanol is to be recovered and preferably ranges from 3 to 5 evaporation stages. The pressure gradation between the evaporation stages is so selected that the boiling point of the liquid stream supplied to the second evaporation stage is lower than the condensation temperature of the vapors from the preceding stage, such that the heat of condensation of the vapors is used to heat the evaporator and the vapors are condensed in the evaporator. The same also applies for the pressure gradation in the subsequent evaporation stages. The vapors obtained in the final evaporator of the multistage evaporation process are condensed in a separate cooler, wherein cooling water is preferably used for condensation of the vapors.

The pressure in the first evaporation stage is preferably selected to be in the range from 3 to 10 bar and particularly preferably 4 to 7 bar. The pressure is so selected that a sufficient pressure and temperature gradient is achieved over the series of evaporation stages and an economic heating medium, preferably steam at a pressure of 4 to 8 bar, may be used to heat the first evaporator. The pressure in the final evaporation stage is preferably selected to be in the range from 0.5 to 2 bar and particularly preferably 0.8 to 1.5 bar.

The pressure is so selected that a sufficient pressure and temperature gradient is achieved over the series of evaporation stages and the vapors from the final evaporation stage may be condensed in an economic manner using cooling water.

In a preferred embodiment of the process according to the invention, each evaporation stage additionally comprises a distillation column with a rectifying section, such that an overhead with a methanol content of more than 90 wt. %, preferably more than 95 wt. %, is obtained in each evaporation stage The vaporous stream produced in the evaporator is supplied to the lower part of the distillation column. The liquid bottoms resulting in the evaporator may optionally also be supplied to the distillation column together with the vaporous stream. The distillation column may take the form of an apparatus separate from the evaporator. Likewise, it is also possible, however, for the evaporator and the associated distillation column to be constructed as one apparatus. At the top of the column, the vapors are removed in vapor form and supplied to the evaporator of the subsequent evaporation stage. A liquid stream of condensed vapors is fed into the upper part of the column, to produce reflux. The stream of condensed vapors used to produce reflux may be taken from the liquid stream which is obtained by condensation of the vapors in the subsequent evaporation stage. Likewise, however, the vapors of all the evaporation stages may also be combined together and the liquid stream for producing reflux may be taken from the mixture of combined vapors. The liquid stream obtained by reflux in the bottom of the column is supplied together with the bottoms from the evaporator to the next evaporation stage.

For the distillation column used in the evaporation stages in this preferred embodiment, the plate number and the reflux ratio are selected in accordance with the composition of the vaporous stream produced in the evaporator and the desired purity of the recovered methanol. The reflux ratio is here defined as the ratio of the mass of the stream fed in in liquid form as reflux to the mass of the vaporous vapors removed at the top of the column. The distillation columns used in the evaporation stages preferably comprise 2 to 10 and particularly preferably 3 to 6 theoretical plates. Preferably, columns are used in the series of evaporation stages which have a plate number which increases over the series. The distillation columns used in the evaporation stages may in principle be of any desired design and may for example take the form of plate columns or of packed columns having regular or irregular packing. The distillation columns in the evaporation stages are preferably operated at a reflux ratio in the range from 0.1 to 1 and particularly preferably 0.2 to 0.6. Preferably, the distillation columns are operated with a reflux ratio which increases over the series of evaporation stages.

The process according to the invention additionally comprises a series of at least 2 distillation stages, wherein in this series the pressure is increased from each distillation stage to the next. Each of the distillation stages comprises a distillation column and an evaporator. The liquid bottoms obtained in the final evaporation stage of the multistage evaporation are supplied to the first distillation stage in the middle portion of the distillation column. The bottoms obtained in the distillation column of the preceding distillation stage is in each case supplied to the second distillation stage and each subsequent distillation stage in a middle portion of the distillation column. In the final distillation stage, the evaporator is heated with a heating medium, preferably with steam. The evaporators of the preceding distillation stages are in each case heated with the vaporous vapors of the distillation column of the immediately subsequent distillation stage. The vapors obtained at the top of the distillation column of the first distillation stage are condensed in a separate cooler, wherein cooling water is preferably used for condensation of the vapors. The number of distillation stages is selected in accordance with the composition of the mixture fed into the first distillation stage and the desired residual methanol content in the bottoms, obtained in the distillation column of the final distillation stage, and preferably amounts to two distillation stages.

The pressure gradation in the series of distillation stages is so selected that the boiling point at the bottom of the distillation column of the first distillation stage is lower than the condensation temperature of the vapors from the distillation column of the second distillation stage, such that the heat of condensation of the vapors from the second distillation stage is used to heat the evaporator of the first distillation stage and the vapors are condensed in the evaporator. The same applies to the pressure gradation between the further distillation stages.

In the first distillation stage, the pressure used is preferably of 0.5 to 2 bar and particularly preferably 0.8 to 1.5 bar, such that a sufficient pressure and temperature gradient is achieved over the series of distillation stages and the vapors arising at the top of the column of the first distillation stage may be condensed economically with cooling water. The pressure in the final distillation stage is preferably selected to be in the range from 3 to 10 bar, particularly preferably 4 to 7 bar, so that a sufficient pressure and temperature gradient is achieved over the series of distillation stages, and an economic heating medium, preferably steam at a pressure of 4 to 16 bar, may be used to heat the evaporator of the final distillation stage.

To produce reflux, a liquid stream of condensed vapors is fed in at the top of the column in the case of each distillation column of the distillation stages. The liquid stream may be taken from the condensed vapors obtained by condensation from the same column. Likewise, however, the vapors obtained in the distillation columns of the series of distillation stages may also be combined together and the liquid stream used to produce the reflux may be taken from the mixture of combined condensed vapors.

For the distillation columns used in the series of distillation stages, the plate number and the reflux ratio are preferably so selected that an overhead with a methanol content of more than 90 wt. % and preferably more than 95 wt. % is obtained in each column. The distillation columns used in the series of distillation stages preferably exhibit a separation effect of 10 to 40 theoretical plates. In principle, all types of distillation column construction are suitable, for example distillation columns with plates or distillation columns with packing, wherein both regular and irregular packing may be used. The reflux ratio in the columns is preferably so selected that it increases over the series of distillation stages from a reflux ratio in the range from 0.3 to 1 in the first column to a reflux ratio in the range from 0.5 to 3 in the final column.

If the mixture containing methanol and water from which methanol is to be recovered still contains intermediate-boiling compounds with a boiling point between the boiling points of methanol and water, the distillation column of the final distillation stage may be provided with a side outlet from which a stream is taken which has an enriched content of the intermediate-boiling compound. For such an embodiment, the distillation column of the final distillation stage may also advantageously take the form of a dividing wall column, in order to obtain a stream with a high concentration of intermediate-boiling compounds.

The process according to the invention is particularly suitable for the recovery of methanol from mixtures containing methanol in a concentration of 70 wt. % and above. The process according to the invention may advantageously be used for the recovery of methanol from mixtures which arise during working up of reaction mixtures which arise when epoxidizing propylene with hydrogen peroxide using methanol as solvent. Such mixtures obtained from working up the reaction mixture from propylene epoxidation typically contain 70 to 90 wt. % of methanol, up to 3 wt. % of intermediate-boiling compounds and up to 3 wt. % of high-boiling compounds, the rest being water. Intermediate-boiling compounds are any compounds whose boiling point lies between the boiling points of methanol and water. High-boiling compounds are any compounds whose boiling point lies above the boiling point of water. To separate such mixtures, the process according to the invention is preferably carried out in such a way that, starting from a mixture with a methanol content of 70 wt. % or higher, a mixture with a methanol content in the range from 40 to 60 wt. % is obtained in multistage evaporation and the mixture is supplied to a series of distillation stages. The operating conditions of the evaporation stages and distillation stages are selected in each case such that overheads with a methanol content of more than 90 wt. % and preferably more than 95 wt. % are obtained.

FIG. 1 shows an embodiment of the method according to the invention with four-stage evaporation and a subsequent series of two distillation stages. The evaporation stages are provided with an in each case separately constructed distillation stage. FIG. 1 shows only the evaporators, distillation columns and condensers required in the process. Pumps, intermediate containers and fittings also required for carrying out the process are not illustrated for the sake of clarity and may be added by a person skilled in the art in accordance with his/her specialist knowledge.

In the most preferred embodiment, the process according to the invention is carried out in an arrangement corresponding to FIG. 1.

The process comprises four-stage evaporation, wherein each evaporation stage comprises a continuous flow evaporator and a distillation column with a rectifying section. The first evaporation stage with the evaporator (1) and the distillation column (2), which comprises a rectifying section with 3 theoretical plates, is operated at a pressure of 5 bar. The second evaporation stage with the evaporator (3) and the distillation column (4), which comprises a rectifying section with 3 theoretical plates, is operated at a pressure of 2.8 bar. The third evaporation stage with the evaporator (5) and the distillation column (6), which comprises a rectifying section with 4 theoretical plates, is operated at a pressure of 1.8 bar. The fourth and final evaporation stage with the evaporator (7) and the distillation column (8) with a rectifying section with 6 theoretical plates is operated at a pressure of 1.0 bar. The fourth evaporation stage additionally comprises a vapor condenser (9).

Downstream of the four-stage evaporation is a series of two distillation stages. The first distillation stage comprises the distillation column (10) with a separation effect of 18 theoretical plates, an evaporator (11) incorporated into the column and a vapor condenser (12) and is operated at a pressure of 1 bar. The second distillation stage comprises the distillation column (13) with a separation effect of 17 theoretical plates and the evaporator (14) incorporated into the column and is operated at a pressure of 4 bar.

The stream (15) from which the methanol is to be recovered and which has a methanol content of 75 to 85 wt. %, an intermediate-boiling compound content of up to 3 wt. % and a high-boiling compound content of up to 1 wt. %, the rest being water, is supplied to the evaporator (1) of the first evaporation stage. The evaporator (1) is heated via the stream (16) by steam under a pressure of 4 bar. The quantity of steam supplied to the evaporator (1) is selected such that approximately 25 wt. % of the stream (15) supplied is evaporated and supplied to the distillation column in vapor form as stream (17). The liquid bottoms arising in the evaporator at a temperature of approx. 118° C. are supplied as stream (18) to the evaporator of the second evaporation stage. Vapor condensate in liquid form is fed in via stream (19) at the top of the distillation column (2), such that a reflux ratio of 0.2 is obtained. The vaporous vapors obtained at the top of the distillation column (2) are supplied as stream (20) to the evaporator (3) of the second evaporation stage as a heating medium. The liquid stream (21) arising at the bottom of the distillation column is supplied, together with the stream (18), to the evaporator of the second evaporation stage.

In the second evaporation stage, the vaporous vapors of the first evaporation stage are condensed in the evaporator (3) and obtained as a liquid vapor condensate (22). The stream (23) evaporated thereby is supplied to the distillation column (4). The liquid bottoms (24) obtained in the evaporator are supplied at a temperature of approximately 100° C. to the evaporator (5) of the third evaporation stage. Liquid vapor condensate is fed in at the top of the distillation column 4 via stream (25) to produce reflux, such that a reflux ratio of 0.25 is obtained. The vaporous vapors obtained at the top of the column 4 are supplied via stream (26) to the evaporator (5) of the third evaporation stage as a heating medium. The liquid product arising at the bottom of the column (4) is supplied as stream (27), together with stream (24), to the evaporator (5) of the third evaporation stage.

The vaporous vapors obtained in the evaporator of the second evaporation stage are condensed in the evaporator (5) of the third evaporation stage and the liquid condensate is combined with the stream (22). The vaporous stream (28) produced in the evaporator (5) is supplied to the distillation column (6). The liquid bottoms of the evaporator (5) are supplied at a temperature of approx. 87° C. to the evaporator (7) of the fourth and final evaporation stage. Liquid vapor condensate is fed in at the top of the distillation column (6) via stream (30), such that a reflux ratio of 0.35 is obtained. The vaporous vapors arising at the top of the column (6) are supplied via stream (31) to the evaporator (7) of the fourth evaporation stage as heating medium. The liquid product obtained at the bottom of the column (6) is supplied as stream (32) together with stream (29) to the evaporator of the fourth evaporation stage.

In the evaporator (7) of the fourth evaporation stage, the vaporous vapors (31) from the third evaporation stage are condensed and the condensate is combined with the stream (22). The product stream (33) evaporated in the evaporator (7) is supplied to the distillation column (8). Liquid vapor condensate is fed in as stream (34) at the top of the distillation column (8), such that a reflux ratio of 0.4 is obtained. The vaporous vapors obtained at the top of the column (8) are condensed as stream (35) in the condenser (9) and the liquid condensate is combined with the stream (22). The liquid product (36) obtained at the bottom of the column (8) is combined with the liquid bottoms of the evaporator (7) and supplied as stream (38) to the first distillation stage.

The liquid stream (38) leaving the multistage evaporation still contains around 45 to 50 wt. % of methanol and is supplied to the distillation column (10) of the first distillation stage. The vaporous vapors (39) obtained at the top of the distillation column (10) are condensed in the condenser (12) and a proportion of the resultant vapor condensate is fed in with stream (40) as reflux at the top of the column (10), such that a reflux ratio of 0.4 is obtained. The remaining proportion of the condensed vapors is combined with stream (22). The liquid bottoms (41) obtained in the distillation column (10) are supplied to the distillation column (13) of the second distillation stage. The evaporator (14) of the second distillation stage is heated via stream (42) by steam under a pressure of 8 bar, such that a bottoms temperature of approx. 143° C. is established. The vaporous vapors obtained at the top of the distillation column (13) are supplied as stream (43) to the evaporator (11) of the first distillation stage as a heating medium. Some of the vapors condensed in the evaporator (11) are recycled as stream (44) as reflux to the top of the column (13), such that a reflux ratio of 1.1 is obtained. The remainder of the condensed vapors is combined with stream (22). At the bottom of the column (13) a stream (45) is obtained, which only has a residual methanol content of less than 0.5 wt. %. The vapor streams (20), (26), (31), (35), (39) and (43) arising in the process are combined after condensation and yield a product stream (46) which contains more than 90 wt. % of methanol and less than 4 wt. % of water.

In this embodiment, the energy requirement for recovering methanol is around 157 kWh/t of methanol. In contrast, the requirement is around 447 kWh/t of methanol for the recovery of methanol in a single column without heat integration. With the process known from WO 02/02544 using two columns with heat integration, the energy requirement is around 246 kWh/t of methanol. The process according to the invention with heat integration both in the multistage evaporation and in the subsequent series of distillation stages thus makes it possible to save approximately 65% of the heating energy required compared with methanol recovery without heat integration. An energy saving of approx. 36% is obtained relative to the method known from WO 02/02544.

What is claimed is:

1. A process for recovering methanol from mixtures containing methanol and water, comprising
   a) a multistage evaporation with a series of at least two evaporation stages, wherein each evaporation stage comprises an evaporator and provides a vaporous overhead product at an operating pressure, said pressure is reduced along said series of evaporation stages and the evaporator of a second evaporation stage and each subsequent evaporation stage is heated with the vaporous overhead product of the preceding stage, and
   b) a series of at least two distillation stages, wherein each distillation stage comprises a distillation column and an evaporator and provides a bottoms product and a vaporous overhead product at an operating pressure, said bottoms product is supplied to the subsequent distillation stage along said series of distillation stages, said pressure is increased along said series of distillation stages and wherein, with the exception of a final distillation stage, in each distillation stage the evaporator is heated by the vaporous overhead product of the subsequent distillation stage, wherein a bottoms product obtained in a final evaporation stage of said multistage evaporation is supplied to a first distillation stage of said series of distillation stages.

2. The process of claim 1, wherein said multistage evaporation comprises 3 to 5 evaporation stages.

3. The process of claim 1, wherein in a first evaporation stage said pressure is in the range from 3 to 10 bar and in a final evaporation stage said pressure is in the range from 0.5 to 2 bar.

4. The process of claim 1, wherein each evaporation stage additionally comprises a distillation column with a rectifying section and wherein in each evaporation stage said vaporous overhead product has a methanol content of more than 90 wt %.

5. The process of claim 4, wherein in each evaporation stage said rectifying section has a separation effect of 2 to 10 theoretical plates and is operated with a reflux ratio in the range from 0.1 to 1.

6. The process of claim 5, wherein said rectifying section has a separation effect of 3 to 6 theoretical plates.

7. The process of claim 5, wherein said rectifying section is operated with a reflux ratio in the range from 0.2 to 0.6.

8. The process of claim 1, wherein said series of distillation stages comprises two distillation stages.

9. The process of claim 6, wherein said rectifying section is operated with a reflux ratio in the range from 0.2 to 0.6.

* * * * *